(12) United States Patent
Boos

(10) Patent No.: US 10,023,199 B2
(45) Date of Patent: Jul. 17, 2018

(54) METHOD AND DEVICE FOR ASCERTAINING A STATE OF DROWSINESS OF A DRIVER

(71) Applicant: Robert Bosch GmbH, Stuttgart (DE)

(72) Inventor: Ronald Boos, Waiblingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/267,343

(22) Filed: Sep. 16, 2016

(65) Prior Publication Data

US 2017/0080947 A1 Mar. 23, 2017

(30) Foreign Application Priority Data

Sep. 23, 2015 (DE) ........................ 10 2015 218 306

(51) Int. Cl.
| | | |
|---|---|---|
| *B60W 40/08* | (2012.01) | |
| *A61B 5/18* | (2006.01) | |
| *A61B 5/11* | (2006.01) | |
| *A61B 3/14* | (2006.01) | |
| *A61B 5/00* | (2006.01) | |
| *B60Q 9/00* | (2006.01) | |
| *B60W 30/18* | (2012.01) | |
| *A61B 5/1171* | (2016.01) | |

(52) U.S. Cl.
CPC .............. *B60W 40/08* (2013.01); *A61B 3/14* (2013.01); *A61B 5/1103* (2013.01); *A61B 5/18* (2013.01); *A61B 5/6893* (2013.01); *A61B 5/7278* (2013.01); *B60Q 9/00* (2013.01); *B60W 30/18* (2013.01); *A61B 5/1171* (2016.02); *B60W 2040/0827* (2013.01); *B60W 2540/26* (2013.01); *B60W 2900/00* (2013.01)

(58) Field of Classification Search
None
See application file for complete search history.

(56) References Cited

U.S. PATENT DOCUMENTS

| | | | | |
|---|---|---|---|---|
| 6,243,015 | B1 * | 6/2001 | Yeo ........................ | G08B 21/06 340/575 |
| 6,346,887 | B1 * | 2/2002 | Van Orden .............. | A61B 5/18 180/272 |
| 8,314,707 | B2 * | 11/2012 | Kobetski .................. | A61B 5/18 340/575 |
| 9,198,575 | B1 * | 12/2015 | Blacutt .................. | A61B 3/113 |
| 9,868,352 | B1 * | 1/2018 | Plummer .............. | B60K 28/066 |
| 9,873,437 | B2 * | 1/2018 | Fung ...................... | B60W 40/08 |
| 2004/0233061 | A1 | 11/2004 | Johns | |
| 2008/0150734 | A1 * | 6/2008 | Johns ....................... | A61B 5/18 340/575 |

(Continued)

*Primary Examiner* — Mussa A Shaawat
*Assistant Examiner* — Abdhesh K Jha
(74) *Attorney, Agent, or Firm* — Norton Rose Fulbright US LLP; Gerard Messina

(57) ABSTRACT

A method for ascertaining a state of drowsiness of a driver of a motor vehicle, movements of at least one eyelid of one eye of the driver being detected, and the state of drowsiness of the driver being determined as a function of the detected movements. It is provided that an instantaneous normal degree of eye opening is determined, that closing movements of the eyelid are monitored based on the normal degree of eye opening, and that the state of drowsiness is determined as a function of the detected closing movements.

10 Claims, 1 Drawing Sheet

(56) References Cited

U.S. PATENT DOCUMENTS

| | | |
|---|---|---|
| 2008/0218359 A1 | 9/2008 | Ishida et al. |
| 2008/0238694 A1 | 10/2008 | Ishida |
| 2009/0040054 A1* | 2/2009 | Wang .................. B60W 30/095 |
| | | 340/576 |
| 2009/0268022 A1 | 10/2009 | Omi |
| 2012/0002843 A1 | 1/2012 | Yoda et al. |
| 2015/0208977 A1* | 7/2015 | Nilsson .................... A61B 5/18 |
| | | 382/103 |
| 2017/0155867 A1* | 6/2017 | Yokota ............... H04N 5/44504 |

* cited by examiner

METHOD AND DEVICE FOR ASCERTAINING A STATE OF DROWSINESS OF A DRIVER

CROSS REFERENCE

The present application claims the benefit under 35 U.S.C. § 119 of German Patent Application No. DE 102015218306.8 filed on Sep. 23, 2015, which is expressly incorporated herein by reference in its entirety.

FIELD

The present invention relates to a method for ascertaining a state of drowsiness of a driver of a motor vehicle, the movements of at least one eyelid of the driver being detected and the state of drowsiness being determined as a function of the detected movements.

The present invention also relates to a device for ascertaining a state of drowsiness of a driver of a motor vehicle, which includes a sensor unit for detecting movements of at least one eyelid of an eye of the driver, as well as a safety unit, which initiates at least one safety measure upon detection of a critical state of drowsiness.

BACKGROUND INFORMATION

Studies have shown that a not inconsiderable number of traffic accidents are caused by drowsiness of the driver. It is therefore very important to be able to detect and, if necessary, also predict the state of drowsiness of a driver. Drowsiness limits the driving fitness to a degree similar to alcohol. A driver who is drowsy is unable to concentrate well, reacts slower and overestimates his/her own abilities. Methods and devices are already in use, which determine the state of drowsiness of the driver as a function of steering angle changes and ability to stay in the lane. Products are also available, which issue a warning when the eye closes. Thus, for example, U.S. Patent Application Publication No. 2004/0233061 A1 describes a monitoring method, in which the movements of an eyelid are monitored in order to detect a blinking by the driver indicating drowsiness.

SUMMARY

A method according to the present invention may have the advantage that the state of drowsiness of the driver is reliably detected by a simple observation of the eye opening and the eyelid movement. For this purpose, it is provided according to the present invention that an instantaneous degree of eye opening is determined and that, in particular, low frequency closing movements of the eyelid are monitored based on the normal degree of eye opening and that, in particular, the state of drowsiness is determined as a function of the closing movements of the eyelid. Thus, the present invention provides that initially the normal degree of an eye opening is determined for the individual driver. This may be determined, for example, from average values of the eye opening measured over a predefinable period of time. The eye opening in this context is understood to mean the distance between the upper eyelid and the lower eyelid when the eyelids are open. The eye opening as so defined differs from person to person. With the method according to the present invention, a normal degree of eye opening is initially ascertained for the present driver of the vehicle. An upper normal position of the eyelid of the driver, in particular, is detected and stored for determining the normal degree of eye opening. Based on the normal position or the normal degree of eye opening, the closing movements of an eyelid are then monitored. The state of drowsiness of the driver is then determined, in particular, as a function of the frequency and the closing distance of the eyelid. Thus, the reference provided for an eyelid movement is not a standardized or reference value, but rather an instantaneously ascertained value, namely, the normal degree of eye opening and the normal position of the eyelids. Because the normal degree of eye opening and the normal position of the eyelids are detected, an automatic adjustment is made to an eye opening of the driver that changes over time, so that the method also ensures a reliable detection/determination of the state of drowsiness of the driver, even over a long period of time.

According to one preferred refinement of the present invention, it is provided that the closing movements of an upper eyelid of the eye are detected. The upper eyelid, in particular, reacts noticeably when the driver is drowsy, in order to keep the eye open, because the eyelid must be held open via muscle contraction, i.e., actively, in order to keep the eye open. If the driver becomes drowsy, he/she attempts to keep the eye open, which may result in the upper eyelid executing micromovements, or "trembling." These micromovements are a clear indication of the occurrence of a critical state of drowsiness. With the advantageous method, these are detected in a simple manner and the state of drowsiness of the driver is reliably determined.

It is provided, in particular, that only closing movements are detected which reduce the eye opening by a maximum of 40%, in particular, by a maximum of 30% based on the normal degree of eye opening. Thus, the micromovements are clearly differentiated from blinking movements of the eyelids. In this way, the method is further optimized.

It is particularly preferably provided that a critical state of drowsiness is detected when the frequency of the detected closing movements exceeds a predefinable limit frequency. Once the limit frequency is exceeded, it is determined that the driver exhibits a critical state of drowsiness and, for example, should be notified of it. An instantaneous state of drowsiness may be determined and the probability of occurrence of a microsleep episode may be predicted as a function of the detected frequency of the closing movements. Accordingly, the driver is displayed an alert warning visually, haptically and/or acoustically, preferably when a critical state of drowsiness occurs, in order to awaken him/her or to notify him/her of his state and, in particular, to prompt him/her to take a break from driving. A safe, automatic stopping of the vehicle may also be initiated as a result of a detected critical state of drowsiness.

It is further preferably provided that an identification of the driver is carried out and the limit frequency is predetermined as a function of the identification. This takes into consideration that a driver exhibits not only different normal degrees of eye opening, but also different reactions in the eyelids during appearances of drowsiness. Thus, the method for determining the state of drowsiness may be further optimized by a targeted monitoring as a function of an identified driver.

According to one preferred refinement of the present invention, it is preferably provided that the closing movements of the eyelid are detected by one, in particular, multiple camera sensors. In this way, the driver is continuously monitored by one or multiple cameras and the movement of the eyelid or eyelids of the driver is ascertained by way of an image analysis. It is provided, in particular, that only one eyelid, namely the upper eyelid, of only one eye of the driver is monitored in order to minimize the computing effort. In order to optimize the method, however, it is preferably provided that the upper eyelids of both eyes of the driver are monitored as described.

An example device according to the present invention is distinguished by a control unit which is specifically configured to carry out the method according to the present invention when used as intended. This yields the above cited advantages.

Additional advantages and preferred features result, in particular, from the description herein.

The present invention is described in greater detail below with reference to the Figures.

DETAILED DESCRIPTION OF EXAMPLE EMBODIMENTS

Figure 1:
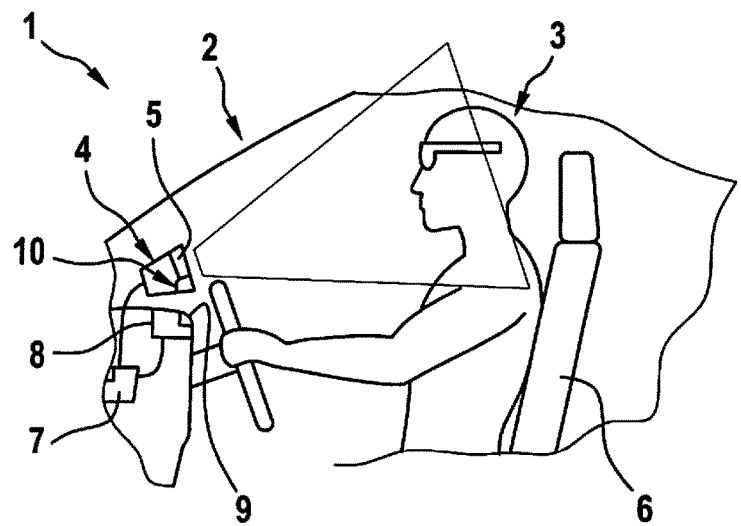
FIG. 1 shows a device for determining a state of drowsiness of a driver.

FIG. 1 shows a simplified depiction of a motor vehicle 1 including a device 2 for communicating a state of drowsiness of a driver 3 of the motor vehicle. Device 2 includes a sensor unit 4 mounted on a dashboard of motor vehicle 2, which includes at least one optical sensor 5, oriented toward driver seat 6, in order to visually detect the face of driver 3. Sensor 5 is designed for such purpose as a video sensor, a camera sensor, an ultrasonic sensor or a thermographic sensor. Sensor unit 4 is connected to a control unit 7, which analyzes the data detected by sensor unit 4, in order to ascertain a state of drowsiness of driver 3. If a critical state of drowsiness is detected, control unit 7 activates a safety device 8, which initiates a safety measure. For this purpose, safety device 8 includes a warning light 9, for example, which is activated when a critical state of drowsiness is detected, in order to visually draw the attention of the driver 3 to his/her critical state of drowsiness.

Figure 2:
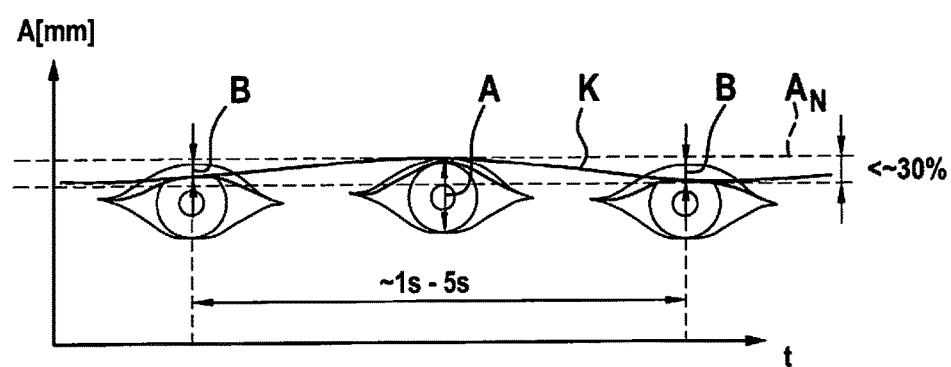
FIG. 2 shows a diagram for explaining the device.

Following is an explanation, with reference to FIG. 2, of how device 2 determines the state of drowsiness of the driver. For this purpose, FIG. 2 shows in a diagram the behavior of an eye of driver 3 detected by sensor unit 4, plotted over time t, for example. By analyzing the image, sensor unit 4 continuously ascertains a degree of eye opening A of an eye of driver 3 from the data of sensor 5. The degree of eye opening results from the distance between an upper eyelid of the eye and a lower eyelid of the eye. If the eye is closed, the distance A equals zero. If the eye is opened, the distance changes to a value greater than zero, the range of the eye opening varying from driver to driver, and thus resulting in variously wide degrees of eye opening. In addition, the degree of eye opening may change over the time of use of motor vehicle 1; if, for example, the driver becomes drowsy, the degree of eye opening decreases over time.

In the present case, therefore, it is provided that a normal degree of eye opening $A_N$ is initially determined. For this purpose, the degree of eye opening of the driver is monitored over a predefinable period of time and from this, the normal degree of eye opening is formed, for example, by averaging the detected values.

Micromovements or closing movements of the upper eyelid are then detected based on the normal degree of eye opening, which reduce the eye opening, based on the normal degree of eye opening $A_N$ by a maximum of 40%, in particular, by a maximum of 30%. In addition, FIG. 2 shows, for example, a movement characteristic curve K of the upper eyelid of the eye of the driver, whose normal degree of eye opening $A_N$ is observed. In the process, control unit 7 analyzes how frequently such closing movements of the upper eyelid occur and calculates herefrom the frequency of closing movements. The frequency may, for example, cover a range of 0.2 Hz to 1 Hz. These low-frequency oscillations of the upper eyelid are used to determine the state of drowsiness of driver 3. The closing movements described arise as a result of muscle fatigue in the upper eyelid. As drowsiness intensifies, the human body struggles against an imminent closing of the upper eyelid, resulting in the occurrence of small closing movements. Thus, these closing movements are an indication of a high level of drowsiness and a sign of an imminent microsleep episode.

Therefore, the detected frequency, with which the described closing movements occur, is preferably compared with a predefinable limit frequency, so that a conclusion may be drawn in a simple manner about the state of drowsiness of driver 3. Driver-related data may also be considered in the process such as, for example, the age of the driver, in order to optimize the analysis of the detected closing movements. An identification of the driver, in particular, takes place via sensor unit 4 itself, which detects preferably the entire head, or the face of the driver, and detects and analyzes on the one hand at least the normal degree of eye opening and the closing movements of one eyelid of an eye and, on the other hand, the facial features of the driver for the purpose of identification.

Driver 3 or the head of driver 3 is preferably detected by multiple sensors 5 of sensor unit 4, so that the face is detected over a wider angle and a better coverage of the driver is ensured. In addition, sensor unit 4 is preferably assigned an illumination unit 10, which illuminates driver 3 when needed in order to improve the detection of an analyzable image by sensor or sensors 5. Illumination unit 10 is, in particular, at least one infrared lamp, which illuminates driver 3 when needed, without blinding the driver. Sensor or sensors 5 preferably has/have a sampling rate of a maximum of 30 Hz. Because it is necessary to detect small movements of the eyelid, sensor or sensors 5 advantageously have a high resolution. A drowsiness index is determined based on the combination of the aforementioned parameters, or other algorithms, in order to arrive at an estimate of the state of drowsiness of the driver. A risk index or the probability of occurrence of a microsleep episode in the next few minutes may also be determined. In this case, the microsleep episode is compared with limit values based preferably on previous tests, in particular, as a function of the frequency and the range of the closing movements B.

If a critical state of drowsiness of driver 3 is detected, safety device 8 is then activated, as described above, to issue a warning signal to driver 3. Alternatively or in addition to the described visual warning of driver 3, it is provided that driver 3 is made haptically or acoustically aware of his/her state. It is also possible that safety device 8 initiates a safe stop of motor vehicle 1 or, to increase safety, prevents motor vehicle 1 from being started.

What is claimed is:

1. A method for ascertaining a state of drowsiness of a driver of a motor vehicle, comprising:
    detecting, by an image sensor, images of an eye of the driver;
    processing, by a processor, the images to determine, for each of the images, a respective distance of an upper eyelid of the eye from a lower eyelid of the eye as represented by the respective image;

for each of the determined distances, determining, by the processor what percentage the respective determined distance is of a predetermined normal degree of eye opening;

filtering out, by the processor, a first subset of the measurements for which the determined percentage is less than a first threshold and a second subset of the measurements for which the determined percentage is greater than a second threshold, the filtering resulting in a remaining third subset of the measurements;

determining, by the processor, a frequency with respect to time at which the measurements of the third subset occur;

determining, by the processor, that the identified frequency is greater than a predetermined threshold frequency corresponding to a trembling eyelid movement caused by drowsiness; and responsive to the determination, outputting, by the processor, at least one of (a) a signal that warns of a critical state of drowsiness and (b) triggers an automatic vehicle driving maneuver.

2. The method as recited in claim 1, wherein the filtering detects closing movements of the upper eyelid that are not complete closures of the eye.

3. The method as recited in claim 1, wherein the first percentage is ≥60%.

4. The method as recited in claim 1, wherein the first percentage is ≥70%.

5. The method as recited in claim 1, wherein an identification of the driver is carried out and the threshold frequency is set as a function of the identification.

6. The method as recited in claim 1, wherein the image sensor includes multiple camera sensors.

7. A device for ascertaining a state of drowsiness of a driver of a motor vehicle, comprising:

an image sensor configured to detect images of an eye of the driver; and a safety device that includes a processor that is configured to:

process the images to determine, for each of the images, a respective distance of an upper eyelid of the eye from a lower eyelid of the eye as represented by the respective image;

for each of the determined distances, determine what percentage the respective determined distance is of a predetermined normal degree of eye opening;

filter out a first subset of the measurements for which the determined percentage is less than a first threshold and a second subset of the measurements for which the determined percentage is greater than a second threshold, the filtering resulting in a remaining third subset of the measurements;

determine a frequency with respect to time at which the measurements of the third subset occur;

determine that the identified frequency is greater than a predetermined threshold frequency corresponding to a trembling eyelid movement caused by drowsiness; and responsive to the determination, output at least one of (a) a signal that warns of a critical state of drowsiness and (b) triggers an automatic vehicle driving maneuver.

8. The method as recited in claim 1, wherein the normal degree of eye opening is an instantaneous normal degree of eye opening determined based on an identification of the driver.

9. The method as recited in claim 1, wherein the signal that warns of the critical state of drowsiness is output.

10. The method as recited in claim 1, wherein the signal that triggers the automatic vehicle driving maneuver is output.

* * * * *